United States Patent
Fischer et al.

(10) Patent No.: US 9,968,384 B2
(45) Date of Patent: May 15, 2018

(54) MEDICAL SCREW DRIVER, SHANK FOR MEDICAL SCREW DRIVER AND METHOD OF INTRODUCING PEDICLE SCREWS

(71) Applicant: Aesculap AG, Tuttlingen (DE)

(72) Inventors: Kay Fischer, Tuttlingen (DE); Sven Krüger, Trossingen (DE)

(73) Assignee: AESCULAP AG, Tuttlingen (DE)

( * ) Notice: Subject to any disclaimer, the term of this patent is extended or adjusted under 35 U.S.C. 154(b) by 37 days.

(21) Appl. No.: 14/747,009

(22) Filed: Jun. 23, 2015

(65) Prior Publication Data

US 2016/0000478 A1    Jan. 7, 2016

(30) Foreign Application Priority Data

Jul. 1, 2014   (DE) ................ 10 2014 109 200

(51) Int. Cl.
| | |
|---|---|
| *A61B 17/70* | (2006.01) |
| *A61B 17/88* | (2006.01) |
| *A61B 17/58* | (2006.01) |
| *A61B 17/00* | (2006.01) |
| *A61B 17/56* | (2006.01) |

(52) U.S. Cl.
CPC ........ *A61B 17/7082* (2013.01); *A61B 17/708* (2013.01); *A61B 17/8816* (2013.01); *A61B 2017/0023* (2013.01); *A61B 2017/564* (2013.01)

(58) Field of Classification Search
CPC .......... A61B 17/7082; A61B 17/8875–17/889; A61B 17/7076; A61B 17/708
See application file for complete search history.

(56) References Cited

U.S. PATENT DOCUMENTS

| | | |
|---|---|---|
| 3,288,184 A | 11/1966 | Kyser |
| 4,779,494 A | 10/1988 | Quach |
| 5,355,752 A | 10/1994 | Keenan et al. |

(Continued)

FOREIGN PATENT DOCUMENTS

| | | |
|---|---|---|
| DE | 102011050996 | 12/2012 |
| WO | 2011043799 | 4/2011 |
| WO | 2014062694 | 4/2014 |

OTHER PUBLICATIONS

German Search Report for German Application No. 10 2014 109 200.7 dated Jan. 30, 2015, including partial translation.

(Continued)

*Primary Examiner* — Jacqueline Johanas
(74) *Attorney, Agent, or Firm* — RatnerPrestia (57) ABSTRACT

A medical screw driver includes a shank having a coupling for a handling member for applying torque to the shank. A screw driver portion can be inserted in a pedicle screw head and transmit torque to the screw head. A sleeve is rotatable about the shank and includes a male thread for coupling to a female thread formed at the pedicle screw head. The sleeve has a first sleeve portion having a first engaging portion and a second sleeve portion having a second engaging portion. The first and second engaging portions engage so that the second sleeve portion can transmit torque to the first sleeve portion, and so that the second sleeve portion can be disengaged from the first sleeve portion and drawn off the shank without having to release the first sleeve portion from the pedicle screw head.

21 Claims, 5 Drawing Sheets

(56) References Cited

U.S. PATENT DOCUMENTS

| | | | |
|---|---|---|---|
| 6,299,616 B1 * | 10/2001 | Beger | A61B 17/7044 606/86 A |
| 6,973,860 B2 | 12/2005 | Nish | |
| 6,997,086 B1 | 2/2006 | Graham | |
| 7,197,968 B2 * | 4/2007 | Bubel | A61B 17/8875 192/56.62 |
| 7,572,264 B2 * | 8/2009 | Null | A61B 17/862 606/104 |
| 8,439,922 B1 * | 5/2013 | Arnold | A61B 17/7082 606/104 |
| 8,814,880 B2 * | 8/2014 | McAllister | A61B 17/86 606/104 |
| 8,900,280 B2 | 12/2014 | Paroth | |
| 9,242,357 B2 * | 1/2016 | Nino | B25B 23/141 |
| 9,572,605 B2 * | 2/2017 | Shipp | A61B 17/7082 |
| 2005/0228400 A1 | 10/2005 | Chao | |
| 2005/0261687 A1 | 11/2005 | Garamszegi | |
| 2008/0200918 A1 | 8/2008 | Spitler | |
| 2008/0254917 A1 * | 10/2008 | Fischer | A63B 69/0075 473/417 |
| 2009/0005787 A1 | 1/2009 | Crall | |
| 2009/0163963 A1 | 6/2009 | Berrevoets | |
| 2009/0264895 A1 | 10/2009 | Gasperut | |
| 2009/0326674 A1 | 12/2009 | Liu | |
| 2010/0211115 A1 * | 8/2010 | Tyber | A61B 17/863 606/305 |
| 2011/0040336 A1 | 2/2011 | Hammill | |
| 2011/0245881 A1 | 10/2011 | Mitchell | |
| 2012/0059385 A1 * | 3/2012 | Lewis | A61B 17/8875 606/104 |
| 2014/0100616 A1 * | 4/2014 | Shipp | A61B 17/7082 606/86 A |
| 2014/0142632 A1 | 5/2014 | Keyer | |
| 2014/0324062 A1 * | 10/2014 | Heuer | A61B 17/7082 606/104 |
| 2015/0119940 A1 * | 4/2015 | Jackson | A61B 17/7076 606/266 |

OTHER PUBLICATIONS

International Preliminary Report on Patentability and Written Opinion for International Application No. PCT/US2013/065076 dated Apr. 21, 2015.

International Search Report for International Application No. PCT/US2013/065076 dated Jan. 9, 2014.

European Search Report dated Nov. 11, 2015 for European Application No. 15172142.0, with English Translation.

* cited by examiner

MEDICAL SCREW DRIVER, SHANK FOR MEDICAL SCREW DRIVER AND METHOD OF INTRODUCING PEDICLE SCREWS

RELATED APPLICATION

This application is the U.S. country equivalent of, and claims the benefit of priority of, German Application No. DE 10 2014 109 200.7, filed Jul. 1, 2014, the content of which is incorporated by reference in its entirety herein for all purposes.

FIELD

The invention relates to a medical or surgical screw driver, a shank for such a screw driver, and a method of introducing pedicle screws.

BACKGROUND

Pedicle screw drivers of the relevant species substantially consist of an outer sleeve for gripping and guiding the instrument, an intermediate sleeve rotatably and movably received by the latter which is made to engage in a head of a pedicle screw as well as a multi-part shank inserted in the intermediate sleeve by which shank the pedicle screw is finally screwed together.

From the disclosure of the document US 2008/0200918 A1 a screw driver comprising an outer protective sleeve is known through the distal aperture of which an intermediate sleeve is inserted. Through a distal aperture of the intermediate sleeve in turn a shank is inserted by means of which a pedicle screw is screwed. A locking means adapted to connect the shank to the intermediate sleeve in a rotationally fixed manner so that inadvertent release of this connection is prevented after arranging the pedicle screw at the screw driver is pushed onto the shank in the axial extension of the protective sleeve at its proximal end. Accordingly, the known screw driver system is designed so that it is assembled successively from the outside to the inside by inserting each successive component to be mounted into the already mounted component through the distal aperture of the latter. As a consequence, dismounting can be carried out in the inverse order and direction only, i.e. such that the screw driver system first has to be separated from the pedicle screw so that the shank can be removed first so as to be able to subsequently dismount the locking means and finally the intermediate sleeve.

The document WO 2011/043799 describes a similar screw driver of the afore-described type for screwing pedicle screws. In this system initially an intermediate sleeve is rotatably and movably introduced into an outer sleeve via the proximal aperture thereof. A two-part initially dismounted shank is received by the intermediate sleeve. A proximal portion of the shank is introduced first via a proximal aperture of the intermediate sleeve into the same.

After that a second portion of the shank is introduced via a distal aperture of the intermediate sleeve into the same and is coupled to the first portion in a rotationally fixed manner. Only now can this system be used for arranging a pedicle screw. Then a distal thread of the intermediate sleeve is screwed to a head of a pedicle screw and the screw engaging element is clamped there between. After screwing the bone screw into the pedicle by the screw driver, the intermediate sleeve is screwed out of the head via a proximal handle and the entire screw driver can be removed while the pedicle screw remains in the body.

Usually set pedicle screws are checked by visual inspection and, respectively, radiographs and are corrected if required. Here the operating surgeon is faced with two problems. On the one hand, the view to the pedicle position is strongly restricted by the comparably bulky system comprising two sleeves each having a proximal handle as well as the shaft received therein. In addition, among various different reasons a plurality of comparatively bulky elements such as those of the screw driver are the reason for undesired artefact formations during X-raying, from which the quality of the photograph suffers and the judgment of the result is impeded. Since in the case of the known systems the screw driver can be uncoupled and removed from the body only as a whole, as a consequence the existing connection between the pedicle screw and the screw driver equally would have to be released. Consequently, for a required correction the screw driver again has to be coupled to the pedicle screw which is detrimental to the bone screw already screwed in and the connection thereof to the bone and which moreover is time-consuming.

Frequently, after screwing in a pedicle screw cement augmentation is carried out by means of cannulated screws to improve fixation thereof in the bone, especially for fixation in the osteoporotic vertebral body. In the known systems it is a drawback that the screw driver first has to be detached and a cement applicator has to be coupled to the bone screw, an injection cannula has to be fastened to the pedicle screw or another sleeve has to be inserted in the pedicle screw so that this connection withstands the pressure developed during cementing. Thus the intervention is extended in time and further cost-intensive instruments are required.

After placing two or more pedicle screws and cementing, where appropriate, it is frequently necessary to reposition the respective carriers of the pedicle screws relative to each other by distracting or compressing and to keep free an access to the operating area so that the operating surgeon is able to work largely unhindered. Points of application for carrying out manipulations are the neck of the bone screw, the outside of the body or head, the inside of the body or head or the Torx (hexagon socket) in the bone screw and, respectively, combinations thereof. Manipulations acting on the body or screw neck are not parallel. Usually parallel distraction/compression is desired, however. A parallel movement is ensured only when the bone screw is connected directly and rigidly to a parallel distractor/compressor. Several systems offer the possibility of blocking the bone screw to the body without making use of the connecting rod and the clamping screw or set screw, by pressing directly onto the insert so as then to act on the body and to be able to perform parallel distraction/compression. This course of action is by far more complicated and is not suited for rapid distraction/compression.

Moreover, in the latter system it is a drawback especially regarding smooth and precise screwing-in that no continuous shank is available. Therefore a certain degree of play always has to be accepted during screwing-in.

Since the known systems both restrict the capability of inspecting the already mounted screws and allow subsequent and usually highly necessary steps such as cement augmentation and distraction/compression by dismounting and mounting of different tools only in an intricate and time-intensive manner, there is a need for action in further developing the screw systems.

SUMMARY

Against this background, the object underlying the invention is to provide a multifunctional shank free from play and suited for cement augmentation, a multi-functional screw driver and a simplified and time-saving method so that pedicle screws can be screwed in reliably and precisely and can be permanently fixed with a minimum of tool changes.

This object is achieved by the features of the screw driver, the shank and the method described herein.

The medical and, respectively, surgical screw driver described herein achieves the object by the fact that the sleeve has a multi-part, especially two-part design and comprises a first distally arranged sleeve portion including a first engaging portion and a second sleeve portion arranged proximally thereto and having a complementary second engaging portion. The two engaging portions are configured so that they can be made to engage such that the second sleeve portion can transmit a torque to the first sleeve portion so as to be capable of coupling the coupling portion provided at the first sleeve portion to the head. On the other hand, the two sleeve portions, more exactly speaking the two engaging portions, can be disengaged, namely without using tools, wherein merely the second sleeve portion can be removed from the first sleeve portion in the axial direction. Hence the second sleeve portion can be drawn off the shank in the proximal direction and can be removed from the shank without having to detach the first sleeve portion from the body or the head of the pedicle screw and without having to abandon the bracing of the screw driver and the pedicle screw.

In other words, the screw driver according to the invention includes a separable sleeve. Each sleeve portion has a different function. The first sleeve portion which can be dimensioned to be small merely serves for coupling the screw driver to the head of the pedicle screw. The second sleeve portion which is used for tightening and bracing the first sleeve portion with the head and, respectively, the pedicle screw and has to be dimensioned to be appropriately larger, usually may have a gripping portion of larger radial dimensions so that it can be manually gripped and rotated more easily, can be removed after bracing so as to grant the operating surgeon a better view onto the pedicle screw and the operating area, respectively.

As the present screw driver replaces a one-part intermediate sleeve known from prior art by a two-part intermediate sleeve consisting of a clamping sleeve (first sleeve portion) and an adapter sleeve (second sleeve portion), the adapter sleeve can be advantageously dismounted at any time. Then merely the clamping sleeve and the shank braced with the pedicle screw via the clamping sleeve are remaining which have a definitely smaller diameter than the entire screw driver and consequently are less bulky so that the operating surgeon's view onto the intervention point is improved. Equally the artefact formation or, in other words, causal relations artificially brought about on X-rays formed due to errors in data collection are reduced, as fewer components can influence the imaging. In this way a diagnosis can be made more rapidly and the quality is equally improved.

Furthermore, the two-part intermediate sleeve is accompanied by the special advantage that even when the adapter sleeve is dismounted the clamping sleeve can remain mounted and consequently the rigid braced connection between the clamping sleeve and the head, on the one hand, and between the shank and the pedicle screw head, on the other hand, is retained. This is time-saving at least when the bone screw would have to be corrected, for in such case merely the shank has to be rotated without a repeated coupling between the pedicle screw and the shank/screw driver system being necessary. It is equally advantageous in this context that, when the bone screw is finally inserted, the adapter sleeve can be easily pushed onto the shank and the second engaging portion of the adapter sleeve can be coupled to the first engaging portion of the clamping sleeve so as to uncouple the shank from the head.

It is a particular advantage of the fact that after dismounting the adapter sleeve the shank is retained in the braced condition with the pedicle screw that almost any type of distractor or compressor and especially parallel distractors and compressors can be connected and required manipulations can be carried out. Hence, after screwing in the pedicle screw, the operating surgeon can transmit forces and/or torques by means of the distractor or compressor in any direction to the bone screw and thus to the bone with an almost unobstructed view to the operating field. Thus after removing the adapter sleeve the distractor or compressor can act directly on the one-part screw driver shank and not on a superimposed sleeve possibly having considerable radial and axial play as in the case of prior art. In this way, a substantially more sensitive manipulation of the pedicle screw and the vertebral body, respectively, can take place.

Hence the screw driver according to the invention simultaneously fulfils the function of a screw driver and of a force transmission member to which almost any instrument suited for manipulation can be connected. Moreover, the invention provided a simple inexpensive instrument which is also easy to mount and which saves time and costs due to its multi-functionality. In addition, the permanent coupling between the shank and the pedicle screw or bone screw prevents the latter from being stained.

Furthermore, the surgical instrument can be disintegrated almost completely despite its multi-functional and partly complex configuration and hence is easy to clean.

Advantageous further developments of the screw driver are also described herein.

In accordance with one aspect, the first and second engaging portions can be configured as corresponding crowns engaging with each other in the axial direction and merely constituting a form closure in the circumferential direction for torque transmission. Such crown can be manufactured in a very simple and thus inexpensive manner. Further, no special tolerances of shape have to be observed so that the adapter sleeve can be engaged in the clamping sleeve any time and as often as required by simply pushing the latter onto the shank until the crowns arranged at the distal end and at the end face or the teeth thereof engage in interstices of the crown of the clamping sleeve. By the way, the crowns prevent the component size from increasing in the radial direction so that in addition no negative influence on the view of the operating field has to be accepted. In other words, the two engaging portions of the two sleeve portions merely serve for transmitting a torque so as to transmit a rotary motion manually applied to the second sleeve portion, especially at a specifically provided gripping portion, to the first sleeve portion and in this way to screw e.g. a male thread portion provided at the first sleeve portion into a female thread provided in the head of the pedicle screw and thus to realize an axial coupling of the first sleeve portion and, respectively, the screw driver to the head and, respectively, the pedicle screw. The two engaging portions are engaged and disengaged by axial displacement of the two sleeve portions toward and away from each other. Instead of crowns, any other geometry is possible which provides a form closure in the circumferential direction between the two sleeve portions. The two engaging portions further can be designed so that in the axial direction they exhibit overlapping over a particular axial length so as to permit torque transmission even if the two sleeve portions are somewhat closer to or spaced somewhat farther from each other.

The shank may include two shank portions adapted to be jointly mounted and the first sleeve portion can be caught in the mounted state between the two mounted shaft portions to be especially not movable in the axial direction. Thus it is achieved that the shank and the first sleeve portion do not only form a functional unit for maintaining the coupling or bracing of the screw driver and the pedicle screw but also a structural unit. This prevents the first sleeve portion and, respectively, the clamping sleeve from inadvertently slipping off the shank. Further the operating surgeon saves the step of mounting the clamping sleeve onto the shank.

In accordance with an alternative or additional aspect, the first sleeve portion can be supported to be axially movable on the shank at least over a predetermined length, with a stop provided in the distal direction ahead of the coupling portion at the shank limiting the axial degree of freedom of the first sleeve portion so that the first sleeve portion can transmit an axial force to the shank in the distal direction, when the shank is coupled to the head of the pedicle screw. A certain axial play of the clamping sleeve allows the screw driver portion being first axially inserted properly and completely into the screw head when the male thread of the clamping sleeve contacts the female thread of the head. In this way the operating surgeon need not simultaneously rotate the adapter sleeve upon inserting the screw driver portion into the screw head.

In order to facilitate the handling of the screw driver an outer sleeve rotatable relative to the sleeve can be detachably mounted, especially pushed, onto the first and/or second sleeve portion for gripping the screw driver. The operating surgeon can better guide and align the screw driver by means of this outer or rotary sleeve which does not co-rotate when the shank or the adapter sleeve rotates.

The outer contours of the first sleeve portion and of the second sleeve portion can be configured so that the outer sleeve rotatable relative thereto is axially caught and, respectively, axially fixed between the two sleeve portions. When the outer sleeve is stationary in the axial direction, this facilitates the fine adjusting of the screw driver. Further, the operating surgeon can apply an axial force to the screw driver via the outer sleeve.

The shank may include at least one continuous internal passage in the axial direction. In this case the shank cannot only be used for screwing the pedicle screw into the vertebra but also for cement augmentation without initially having to remove the screw driver and to couple a different instrument to the pedicle screw. The afore-described construction of the clamping sleeve which upon screwing into the head at the same time tightly braces the shank via its stop is further especially advantageous, because a safe coupling between the pedicle screw and the passage outlet opening which withstands the pressure of the cement upon injection is thus provided at the distal end of the shank. Hence the shank can serve as an injection cannula, if cement augmentation is required or desired.

A screw driver of this design permits great time saving, especially when a plurality of pedicle screws has to be screwed in and cemented. This is both in accordance with the patients regarding their health and in accordance with the hospital regarding operating times.

Since the screw driver according to the invention can be completely dismounted, especially the rotary mechanism consisting of the adapter sleeve and the outer sleeve can be removed from the shank, the shank may be in the form of a one-way element (single-use element) when used for cement injection. Since during cementing cement always remains within the shank, the shank having a comparatively simple structure and thus being less expensive can be disposed of by reason of non-avoidable cement residues which are extremely difficult to remove, whereas the other more complicated and expensive elements can be reused (multi-use element).

In order to produce a safe and clean connection between the shank acting as injection cannula and, respectively, the passage provided therein and a cement applicator, the shank furthermore can include a connecting system, preferably Luer system, at its proximal end portion. The use of this standardized interface permits an even simpler and quicker connection of the injection cannula to the cement applicator so that the already screwed in and cannulated bone screw can be cemented in the bone. It is not important in this context whether a Luer lock, lug, plug or slip is used. As a matter of course, the shank may include any other common coupling portions, unless they obstruct a proximal removal of the adapter sleeve.

The second sleeve portion at the shank can be detachably lockable for axial securing. This ensures that the second sleeve portion and the adapter sleeve, respectively, is not inadvertently axially displaced during rotation and the two engaging portions are disengaged. Especially a bar element provided at the second sleeve portion and biased in the radial direction may be provided which automatically engages in a peripheral groove formed at the shank and forms an axial form closure. This locking can be manually detachable, e.g. by means of a press button.

In order to prevent inadvertent release of the coupling between the screw driver and the pedicle screw by rotating the adapter sleeve a rotary locking means, especially a shut-off valve, can be provided which is adapted to be brought between a rotary position in which the second sleeve portion is rotatable relative to the shank and a locking position in which the second sleeve portion is not rotatable relative to the shank. Said rotary locking means thus can be appropriately brought into the locking position after completed coupling and bracing between the screw driver and the pedicle screw.

The object underlying the invention is also achieved by a shank according to the invention which is adapted especially for a medical screw driver in accordance with any one of the afore-mentioned aspects. In the area of its proximal end portion such shank includes a coupling portion for a detachable handling member for applying a torque to the shank and at the distal end portion thereof a screw driver portion, especially including a Torx or hexagon socket profile, is provided which is adapted to be inserted in an appropriate seat at the screw head of the pedicle screw and can transmit a torque applied to the shank to the screw head. In the axial direction the shank further comprises a continuous internal passage, with a connecting system, preferably Luer system, being provided at the proximal end portion of the shank for connecting a cement applicator to the passage.

Such shank can be used especially multi-functionally and is not only suited for screwing in a bone or pedicle screw but also for injecting cement through the internal passage into the bone or pedicle screw. Thus no change of instruments is necessary, which does not only save time for the operating surgeon but also facilitates the surgical intervention, as no second instrument has to be coupled to the pedicle screw.

Another aspect of the invention relates to a method for introducing mono- or poly-axial pedicle screws into a vertebral body using a medical screw driver according to the afore-mentioned type. The method comprises the following steps of: inserting the screw driver portion in an appropriate seat at the screw head of the pedicle screw; coupling and bracing the first sleeve portion with a head of the pedicle screw and the screw driver portion with the screw head by rotating the second sleeve portion; and removing the second sleeve portion from the shank in the proximal direction while maintaining the bracing of the first sleeve portion with the head of the pedicle screw and of the screw driver portion with the screw head.

In accordance with the method according to the invention, part of the sleeve, more exactly speaking the second sleeve portion and, respectively, the adapter sleeve can be removed from the screw driver and from the operation field, respectively, without abandoning the connection free from play between the screw driver and the pedicle screw, whereby, on the one hand, the view onto the operation field by the possibly bulky adapter sleeve is improved and, on the other hand, undesired artefact formations during X-raying can be avoided or at least reduced during the intervention. As required, after screwing in the pedicle screw the adapter sleeve and the outer sleeve can be dismounted so as to improve the view onto the screwed-in pedicle screw.

When the shank of the medical screw driver includes a continuous internal passage in the axial direction and at the proximal end portion of the shank a connecting system for connecting a cement applicator to the passage is provided, the method further can comprise the steps of: coupling a cement applicator to the connecting system; and injecting cement via the passage into the pedicle screw. In this way the operation can be further facilitated and also shortened as a change of instruments can be saved.

After removing the adapter sleeve and possibly together with the outer sleeve, the method can comprise the following steps of: arranging distractors and, respectively, compressors at each of the shank or the first sleeve portion of two or more screw drivers coupled to two or more pedicle screws; and carrying out a distraction or compression, especially a parallel distraction or compression. As already described in the foregoing in relation to the screw driver, this, too, broadens the spectrum of application and the flexible use of the screw driver according to the invention and of the appropriate method of introducing pedicle screws according to the invention.

It has to be noted in this context that, assuming that the pedicle screw has not yet been satisfactorily screwed into the pedicle, the operating surgeon can remove the rotary mechanism as often as required and, preferably after inspection by means of X-rays or the like, re-couple the same to the shank or the clamping sleeve so as to correct the result of screwing. The operating surgeon does not start taking the afore-described steps for cement augmentation of the pedicle screw, if the pedicle screw is to be cemented, unless an optimum screwing result has been reached. Alternatively, it can equally be started to connect distractors and, respectively, compressors without any cement augmentation.

In this way, an especially advantageous method is disclosed according to which the entire procedure of placing a pedicle screw can be carried out by a multi-functional screw driver. It is of special advantage in this case that two steps which have been absolutely necessary for cementing so far, namely dismounting the screw driver and mounting a cement applicator, are omitted. Equally the cement applicator need not be dismounted so as to connect a distractor or compressor. It is rather possible now to connect the distractor or compressor directly after cementing and hardening of the cement to the shank which is still provided and braced with the pedicle screw, preferably to the clamping sleeve, and to carry out the desired manipulations, especially parallel manipulations.

DETAILED DESCRIPTION

Figure 1:
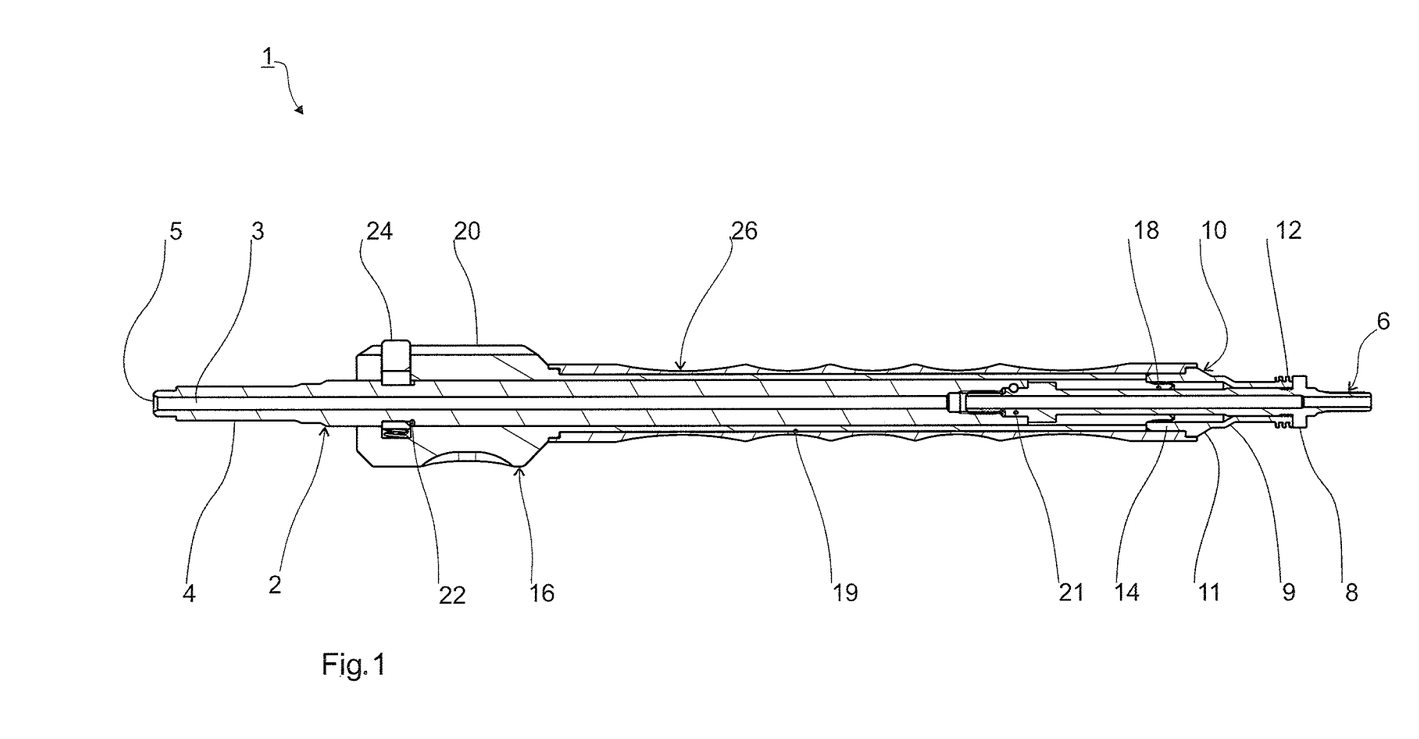
FIG. 1 shows a cross-sectional view of a screw driver system in accordance with a preferred embodiment of the invention.

In FIG. 1 a screw driver system 1 comprising a shank 2 is shown including at its one axial and, respectively, proximal end (left side in FIG. 1) a coupling portion 4 to be coupled to a handle (not shown) and configured as a multi-sided profile and including at its other axial and, respectively, distal end (right side in FIG. 1) a screw driver portion 6 suited for torque transmission and preferably configured as Torx profile or hexagon socket profile. A stop 8 radially extended vis-à-vis an outer shell surface of the shank 2 is proximally connected to said screw driver portion. A standardized connecting system, preferably a Luer system 5 is proximally connected to the multi-sided profile. Furthermore, a through-passage or axial bore 3 is passed through the shank 2 along its longitudinal axis.

As further illustrated in FIG. 1, two components are integrated at a joint 21 to the shank 2. It is essential in this context that the shank 2 is provided in total as an integral component free from play. This can be achieved by a one-piece material, the shank being manufactured as a one-piece member, or by connecting at least two parts by common connecting means.

A first sleeve portion and, respectively, a clamping sleeve 10 is arranged coaxially on the shank 2 and is both axially movable and rotatable. The axial degree of freedom of the clamping sleeve 10 is limited by the stop 8 toward the distal end. With a shank joined from plural parts the clamping sleeve 10 is preferably arranged before the final assembly of the shank 2. With a shank formed of a one-piece material the clamping sleeve is mounted or shrunk by pushing the same onto the multi-sided profile 4 up to the stop 8. At the distal end of the clamping sleeve 10 a male thread 12 is formed. In the proximal direction the clamping sleeve 10 is radially extended in steps via two truncated portions 9 and 11. A first engaging portion 14 in the form of a crown and suited for torque transmission is connected to the proximal one 11 of these two portions. The engaging portion has a smaller outer diameter than the proximal portion 11 so that a proximal annular end face 15 in the form of a shaft shoulder is retained at the same. In other words, starting from the proximal annular end face 15 at least three, preferably four projections of the crown equally distributed along the periphery extend in the axial direction and form the first engaging portion 14 of the clamping sleeve 10.

The shank 2 is coaxially encompassed by a detachable adapter sleeve 16 which is rotatably arranged on the shank 2 like the clamping sleeve 10. The adapter sleeve 16 can be pushed from the proximal end of the shank 2 up to the clamping sleeve 10, with a second engaging portion 18 being formed at its distal end complementary to the first engaging portion 14. The second engaging portion 18, too, is in the form of a crown suited for torque transmission and is configured as coupling portion. The engaging portions 14, 18 are engaged at the end face.

Starting from the second engaging portion 18, a substantially cylindrical sleeve portion 19 of the adapter sleeve 16 having a circular cross-section extends proximally and is converted via a comparatively short conical portion into a handle portion 20 for gripping and rotating the adapter sleeve 16, which handle portion has definitely larger radial dimensions than the sleeve portion 19 and plural flattened gripping portions or recessed grips provided in the circumferential direction.

The shank 2 penetrates the handle portion 20 so far that its multi-sided profile 4 projects from the adapter sleeve 16 and an operating handle can be coupled to the multi-sided profile 4 so as to transmit a torque to the shank 2 and consequently to a screw coupled to the Torx profile of the engaging portion 6.

As is further illustrated in FIG. 1, spaced apart from the multi-sided profile 4 in the distal direction, the shank 2 includes a peripheral groove 22 provided in the area of the handle portion 20 in the mounted state of the adapter sleeve 16. At an internal portion in the radial direction the handle portion 20 is provided with a generally known locking device engaging in the peripheral groove 22 and thus constituting a positive axial lock for the adapter sleeve 16 on the shank 2. More exactly speaking, it is a locking, such as a perforated disk, movably supported in the handle portion 20 in the transverse direction and biased via a spring or the like in the transverse direction which can be released by pressing the locking or a push button 24 against the spring bias, thus causing the locking device and the peripheral groove 22 to be disengaged and the adapter sleeve 16 to be proximally withdrawn and removed from the shank 2.

In order to be able to grip and guide the screw driver system 1, a rotation-symmetric ergonomically shaped rotation sleeve and, respectively, outer sleeve 26 is coaxially pushed onto the adapter sleeve 16. The outer sleeve 26 by each of its end faces distally abuts against the clamping sleeve 10 and proximally abuts against the adapter sleeve 16. More exactly speaking, it encloses the first engaging portion 14 and there abuts against the annular end face 15 of the clamping sleeve 10 by its distal end face. The opposed front side of the outer sleeve 26 constitutes an axial/proximal stop to which the adapter sleeve 16 is adjacent by its handle portion 20. The rotary sleeve 26 is rotatable relative to the adapter sleeve so that the screw driver system 1 can be held while the adapter sleeve 16 or the shank 2 is rotated. After removing the adapter sleeve 16 the rotary sleeve 26 can be withdrawn and removed from the shank 2 equally in the proximal direction and can be pushed onto the shank 2 before pushing on the rotary sleeve, respectively.

Figures 2A, 2B:
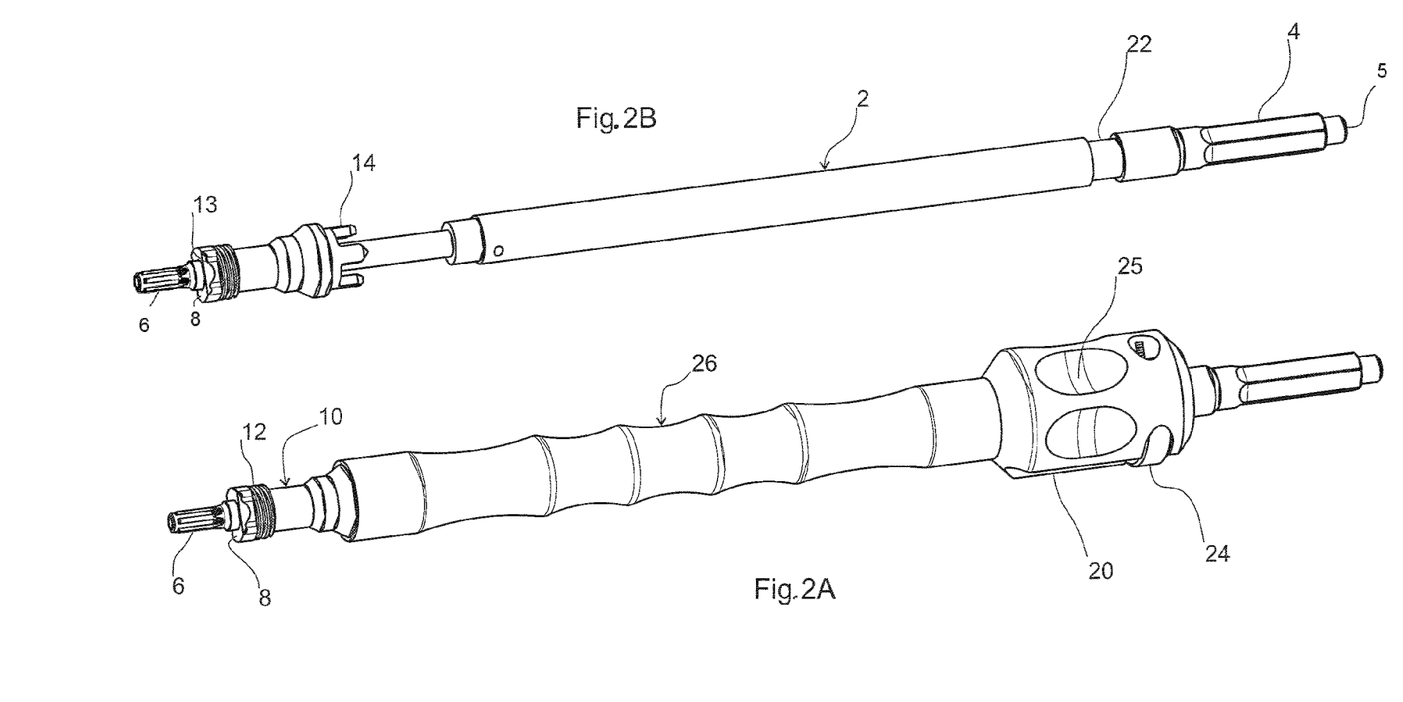
FIG. 2A shows a perspective view of the screw driver system according to the preferred embodiment of the invention.
FIG. 2B shows a perspective view of the screw driver system including dismounted rotary mechanism in accordance with the preferred embodiment of the invention.

FIG. 2A shows an isometric view of the screw driver system 1 in which the multi-sided profile 4 and the push button 24 integrated in the handle portion 20 are illustrated.

Moreover, the recesses or recessed grips 25 cited already before are provided in the handle portion 20 so as to obtain better handling. At the axial end of the shank 2 opposed thereto the Torx profile 6 is provided to which the stop 8 is connected in the proximal direction. On two sides opposed in the radial direction the stop 8 includes portions 13 having flattened areas up to the peripheral shell surface of the shank 2 on which a curved outer contour is formed the outer diameter of which is smaller than that of the male thread 12. In the ideal case the outer diameter of the flattened area 13 is at most as large as the core diameter of the thread portion 12. This has the effect that the male thread 12 of the clamping sleeve 10 radially projects from the clamping sleeve 10 at least in the flattened areas 13 of the stop 8 so that it can be screwed into a female thread 38 (cf. FIG. 3) of a head 36. Moreover, the curved outer contour of the flattened areas 13 engages in respective complementary contours at inner walls of the head 36 so as to establish a connection between the shank 2 and the pedicle screw 30 largely free from play. In addition, in this way a radial lock is realized between the shank 2 and the head 36.

It is further evident that the outer sleeve 26 encompasses the shank 2 as well as the clamping sleeve 10 and the adapter sleeve 16 from the handle portion 20 to the shaft shoulder 15 of the clamping sleeve 10 arranged distally to the first engaging portion 14.

FIG. 2B illustrates an isometric view of the screw driver system 1 in which the rotary mechanism, i.e. the adapter sleeve 16 and the outer sleeve 26 are uncoupled. In addition, here the circumferential groove 22 of the shank 2 is visible into which the locking device (not shown) engages and thus realizes the axial lock between the shank 2 and the adapter sleeve 16.

Figure 3:
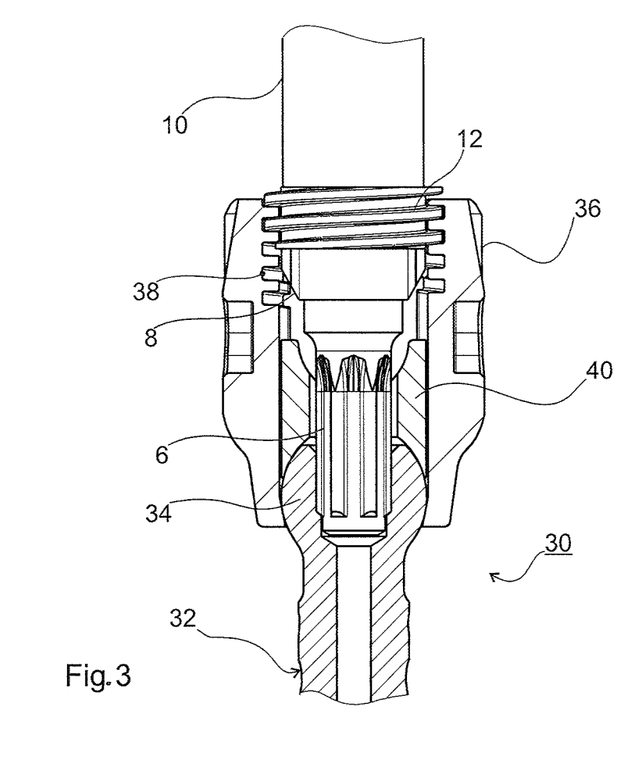
FIG. 3 shows a partly cut partial side view of the screw driver system comprising a poly-axial pedicle screw according to the preferred embodiment of the invention.

FIG. 3 shows a partly cut partial side view of a screw driver system 1 mounted with a poly-axial pedicle screw 30. The pedicle screw 30 is composed of a bone screw 32 which is preferably movably received with its spherical screw head 34 by an axial/distal end portion of the head 36 and an insert 40 attached to the screw head 34. As the male thread 12 of the clamping sleeve 10 is screwed into the female thread 38 provided at the proximal end of the head 36, the Torx profile 6 is inserted in a corresponding engaging portion provided for this purpose and configured as Torx profile in the screw head 34. The Torx profile 6 is guided in the insert 40 by an axial through-bore.

Figure 4A:
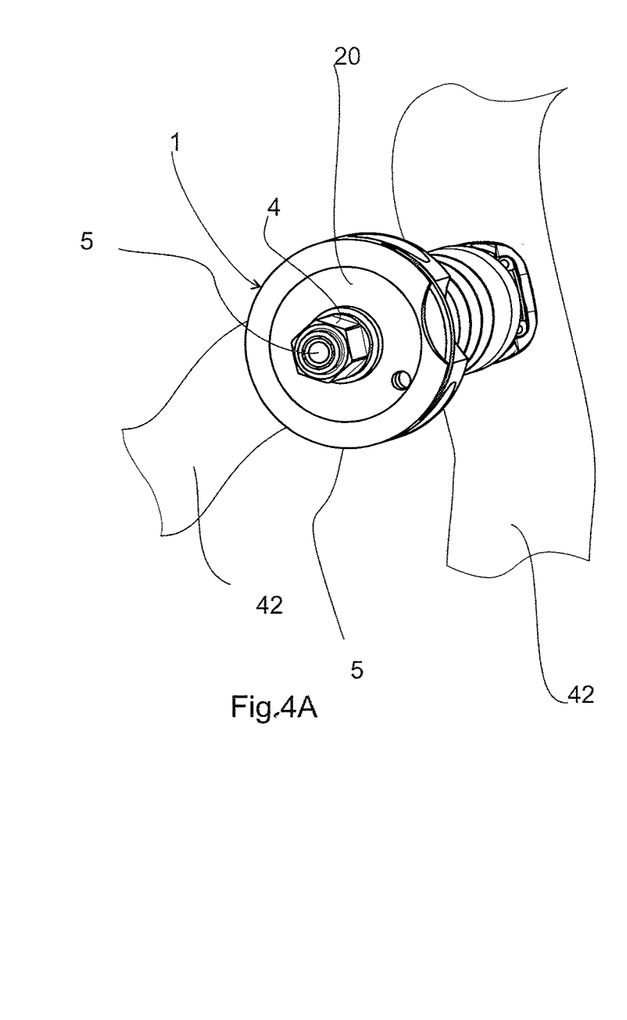
FIGS. 4A and 4B illustrate in respective top views the screw driver system screwed into a vertebra without and with a rotary mechanism.

FIG. 4A shows a top view of a screw driver system 1 which is braced with the pedicle screw 30 (not shown) screwed into a vertebra 42. Here merely the Luer-system 5, the multi-sided profile 4 and a proximal end face of the handle portion 20 are evident. However, the view is otherwise covered by the comparatively bulky handle portion 20 of the adapter sleeve 16, which impedes the operating surgeon to check a screwed condition of the pedicle screw 30 in the vertebra 42.

Figure 4B:
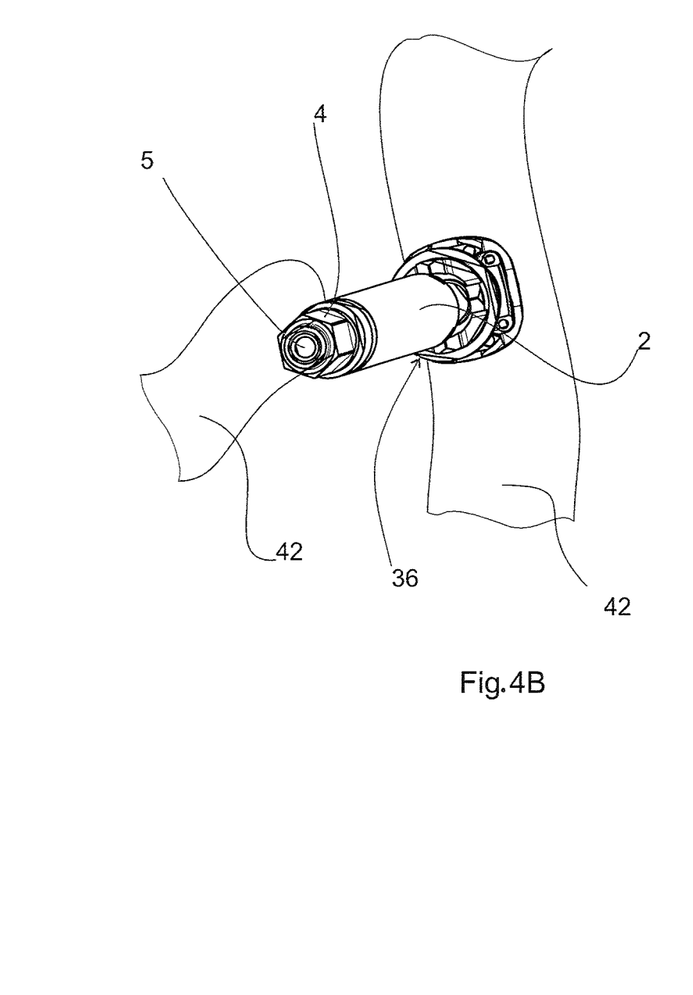

On the other hand, in FIG. 4B the rotary mechanism is proximally dismounted after screwing the pedicle screw 30 into the vertebra 42. Therefore the view in the top view along the shank 2 up to the pedicle screw 30 is unobstructed so that the operating surgeon has an almost unobstructed vision up to the head 36.

Figure 5A:
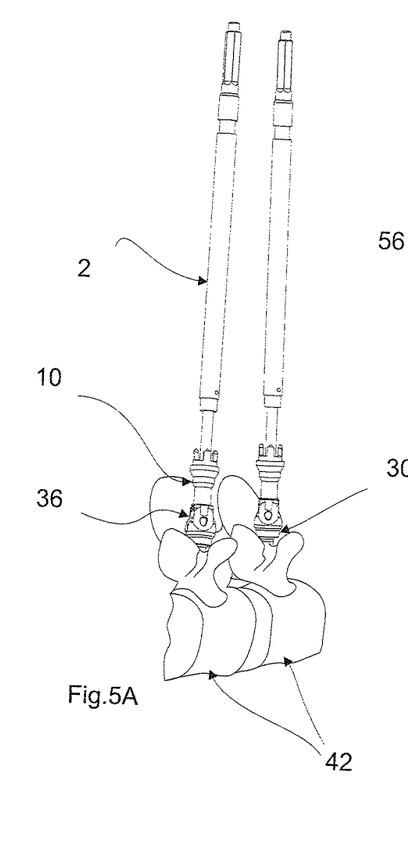
FIGS. 5A and 5B illustrate in perspective views two screw driver systems with the rotary mechanism being dismounted, each being screwed into a vertebra, with and without an exemplary parallel distractor/parallel compressor being coupled thereto.

FIG. 5A exemplifies a perspective view of two screw driver systems according to the invention with dismounted rotary mechanism, each being braced with the pedicle screw 30 screwed into the vertebra 42. This view again clearly illustrates in which way the clamping sleeve 10 is screwed into the head 36 and braces the shank 2 with the pedicle screw 30 by this connection.

Figure 5B:
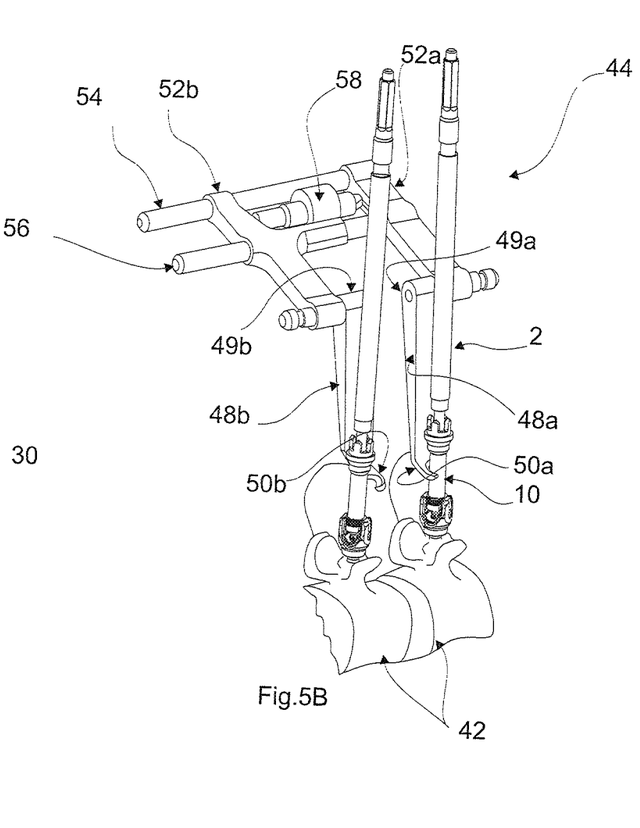

FIG. 5B shows a parallel distractor/compressor 44 coupled to the two screw driver systems of FIG. 5A (hereinafter referred to as "distractor") which is suited for both parallel distraction and compression. The distractor 44 includes two arm portions 48a and 48b which at their free ends encompass the clamping sleeve 10 via a respective coupling portion or gripper 50a, 50b in an area between the truncated portion 9 and the male thread 12. The other end of the one arm portion 48a is connected to a first force transmission element 52a of the distractor 44 via a link 49a and the other end of the other arm portions 48b is connected to a second force transmission element 52b via a further link 49b. To the first force transmission element 52a two guide rails 54 and 56 substantially extending in parallel are connected, the one axial end thereof being connected to the force transmission element 52a extending substantially in parallel thereto. Via the free axial end of the guide rails 54, 56 the second force transmission element 52b is pushed onto the two rails 54, 56. In this way the force transmission elements 52a, 52b are movable relative to each other in a translational manner. Along the direction of translation a force application element 58 is inter-connected between the two force transmission elements 52a, 52b. As the operating surgeon mechanically or electrically (not shown) shortens or extends the force transmission element 58 over an effective length, a force is exerted on the two force transmission elements 52a, 52b and their relative distance is varied. This force is transmitted to the arm portions 48a, 48b via the links 49a, 49b. Since the arm portions are engaged in the clamping sleeves 10, this force is transmitted at the points of application of the grippers 50 to the clamping sleeves 10 and consequently to the bones.

It is noted in this context that the representations in FIGS. 5A and 5B were restricted to only two screw driver systems for the purpose of representation. Therefore it is equally possible that more than two pedicle screws 30 at a time braced with a shank 2 are screwed to different bones, preferably vertebras 42. Also, the distractor 44 may include more than two coupling arms 46 each being coupled to a shank 2 and, respectively, a clamping sleeve 10.

Hereinafter it will be described in which way the screw driver 1 according to the invention is used. It is especially shown that apart from the function of screw driver the screw driver 1 at the same time has the function of a cement injection cannula and serves as force transmission member for distractors and, respectively, compressors.

In order to couple a pedicle screw 30 to the screw driver 1 according to the invention the following steps can be taken:

First the shank 2 is prepared so that the clamping sleeve 10 is coaxially pushed onto the shank 2 and is arranged proximally from the stop 8. For this purpose, either the clamping sleeve 10 is pushed onto the shank 2 or it is already preassembled on the shank 2.

Subsequently, the outer sleeve 26 is attached to the adapter sleeve 16, more exactly pushed over the crown 18 of the adapter sleeve 16 onto the latter, and both are jointly pushed from the proximal side or from behind via the multi-sided profile 4 onto the shank 2 until the crown 18 of the adapter sleeve 16 and the crown 14 of the clamping sleeve 10 are axially engaged and the locking device provided radially inside the adapter sleeve engages in the peripheral groove 22 of the shank 2 and thus axially fixes and secures the adapter sleeve 16 vis-à-vis the shank 2. The outer sleeve 26 then is axially caught between the adapter sleeve 16 and the clamping sleeve 10, but it is rotatable relative to the same.

As an alternative, also the outer sleeve 26 can first be pushed onto the shank 2 and then the adapter sleeve 16 can be pushed onto the shank 2 and into the outer sleeve 26.

When the screw driver portion 6 is inserted in an appropriate screw driver seat (e.g. Torx or hexagon socket) in the screw head 34 of the pedicle screw 30 so that the stop 8 immerses between the two flanks of the head 36 and accordingly the adapter sleeve 16 and via the latter the clamping sleeve 10 is rotated, the male thread portion 12 provided at the distal end of the clamping sleeve 10 is screwed into the corresponding female thread 38 of the head 36 of the pedicle screw 30. Since the axial degree of freedom of the clamping sleeve 10 is limited during screwing into the head 36 by the stop 8 provided at the distal end of the shank and the distal end of the screw driver portion 6 presses against the bottom of the screw driver seat formed in the screw head 34, further screwing of the clamping sleeve 10 into the head 36 causes the head 36 to increasingly remove from the screw head 34 and finally the head 36 and the screw head 34, the clamping sleeve 10 and the head 36 and the screw driver portion 6 and the screw head 6 to be braced with each other free from play.

Preferably, the clamping sleeve 10 is supported on the shank 2 not only rotatably but also axially movably so that it can deflect in the axial direction somewhat to the rear, i.e. in a direction opposed to the stop 8, as otherwise the two thread portions 12 and 38 would prevent the screw driver portion 6 from being completely axially inserted in the screw driver seat without simultaneously rotating the adapter sleeve 16 and, respectively, the clamping sleeve 10. With axial freedom of movement of the clamping sleeve in a first step the screw driver portion 6 can be completely introduced and in a second step the clamping sleeve 10 can be screwed into the head 36. The engaging portions of the adapter sleeve 16 and of the clamping sleeve 10 and, respectively, the crowns 18 and 14 then are preferably configured so that they overlap each other in the axial direction such that the clamping sleeve 10 can be axially moved relative to the adapter sleeve 16 without losing the engagement and the form closure in the direction of rotation.

Through the shape of the stop 8 and interaction thereof with the flanks of the head 36 the shank 2 and the head 36 are coupled in a rotationally fixed manner so that apart from forces also moments can be transmitted by manipulations at the shank 2 and, respectively, at the clamping sleeve 10.

At the proximal multi-sided profile portion 4 serving as coupling for a handle a handle or other operating handle for rotating the shank 2 can be arranged so as to screw the pedicle screw coupled to the screw driver 1 free from play into a vertebral body. While the operating surgeon rotates the handle by the one hand, he/she can hold and align the entire instrument and, respectively, the screw driver 1 by the other hand by gripping the relatively rotatable outer sleeve 26 until the bone screw 32 is screwed into the vertebra 42 to the desired depth. For checking the result the handle can be removed at any time and the rotary mechanism consisting of the adapter sleeve 16 and the outer sleeve 26 can be dismounted to check the position of the bone screw 32 by X-rays.

It is important for subsequent cement augmentation and/or distraction or compression that the axially fixed connection between the screw driver 1 and the pedicle screw 30 is retained.

As the shank 2 is provided with a continuous and internal passage 3 extending over the entire axial length thereof, the shank 2 itself can be used for cement augmentation. Thus directly after screwing in the pedicle screws, cement can be injected into the cannulated pedicle screw 30 via the shank 2 without change of instruments, for which purpose merely a cement applicator has to be connected to the proximal end of the shank 2 and, respectively, the Luer connection 5. Alternatively, a cannula can be inserted in the passage or the through-bore 3 before. The bracing of the shank 2 and the pedicle screw 32 maintained via the clamping sleeve withstands the pressure of cementing.

After placing pedicle screws and cementing, where appropriate, for repositioning frequently distraction or compression is carried out. The screw driver 1 according to the invention is designed so that it establishes a rigid connection to the bone screw and the shank 2 offers a contact surface for all types of distractors/compressors. In order to be able to directly act on the shank 2 by the distractors/compressors, the adapter sleeve 16 and the outer sleeve 26 can be dismounted from the shank 2 without abandoning the bracing of the screw driver 1 and the pedicle screw 30. The adapter sleeve 16 and the clamping sleeve 10 are not fixedly, especially not axially, connected to each other, but are merely engaged via the crowns 14 and 18. Thus the clamping sleeve can be axially drawn off the clamping sleeve 10 and off the shank 2 after releasing the axial lock via the locking device, while the clamping sleeve 10 maintains the bias in a self-locking manner.

Hence the construction is designed so that the screw driver 1 is still safely braced, despite the dismounting of the two sleeves 16 and 26, via the clamping sleeve 10 retained on the screw driver 1 and forces and/or torques can be transmitted in each direction which permits minor derotations while simultaneously an unobstructed view to the operation field is permitted.

After removing the adapter sleeve 16 and the outer sleeve 26, distractors/compressors, especially parallel distractors and/or compressors, can be mounted on the shank 2 or on the clamping sleeve 10 braced with the shank 2 so that distraction or compression free from play can take place. Alternatively, a coupling for e.g. CLR retractors can be provided at the shank 2.

After completed cementing and/or distraction or compression, the screw driver 1 can be uncoupled from the pedicle screw 30 by pushing the adapter sleeve 16 together with the outer sleeve 26 axially onto the shank 2 again and rotating the clamping sleeve 10 out of the head 36 again via the adapter sleeve 16 and the engagement or toothing of the crown 18 of the adapter sleeve 16 and the crown 14, while the bracing of the screw driver 1 and the pedicle screw 30 is released. After that, the screw driver 1 can be removed from the operating field so as to be able to subsequently take further operating steps such as inserting a connecting rod in the pedicle screws etc.

Then the screw driver can be dismounted and cleaned again. After completed cementing directly via the shank 2 the latter can be disposed of and the other components, i.e. the adapter sleeve 16, the outer sleeve 26, the clamping sleeve 10 (if adapted to be dismounted from the shank 2) and the handle can be cleaned and are re-usable with a new shank.

The screw driver system according to the invention is not restricted to the afore-described embodiment.

For example the assembly of the adapter sleeve 16 and the outer sleeve 26 to the shank and the thus possible bracing of the screw driver 1 with the pedicle screw 30 can also be performed after screwing in the pedicle screw via the handle and the shank 2. After completed bracing the adapter sleeve 16 and the outer sleeve 26 can be dismounted and remounted at any time.

The crown can have any number of projections in the form of teeth which may have axial lengths deviating from each other so as to render coupling of both complementary engaging portions in a more uniform and simple manner. In this way engagement of the teeth not at the same time but successively is achieved.

The handle portion of the adapter sleeve has a substantially cylindrical shape according to the illustrated embodiment. However, it can have any other shape such as a spherical shape by which the handle portion can be safely gripped and rotated by an operating surgeon.

The outer sleeve can equally exhibit any contour other than the shown one as long as an operating surgeon thus can properly hold and guide the screw driver system. A central area of the outer sleeve in the axial direction can be spherical so that it can be better gripped by one hand.

Although the shank is provided with a multi-sided profile for coupling a handle, this is not absolutely necessary, however, and it can also be in the form of an involute spline or the like.

The Torx profile at the distal shank end can be, in deviation of the shown shank, a hexagon socket, slotted or cross-head profile.

Alternatively, a cannula by which the cement can be injected into the bone can be inserted through the shank up to the bone screw. In this way the shank can be re-used.

The invention discloses a screw driver for introducing mono-axial and poly-axial pedicle screws which at the same time fulfils the function of a cement injection cannula and moreover serves as force transmission member to which distractors and compressors of almost any design can be easily coupled. The screw driver includes an intermediate sleeve consisting of the adapter sleeve and the clamping sleeve as well as a one-part continuous shank having an inner through-bore. This permits maintaining a braced coupling of the screw driver to a pedicle screw during the entire operation of placing a bone screw. Moreover, all elements such as the adapter sleeve and the outer sleeve can be uncoupled at any time so as to improve the view as well as the quality of X-rays. Furthermore, the cement augmentation can be carried out by the shank acting as cement augmentation sleeve in the braced condition, and subsequently distractors and compressors can be coupled to the braced shank for the purpose of manipulation, especially in the case of parallel manipulations. In this way forces and moments can be transmitted without any change of instruments and loss of time. For this purpose, specific coupling geometries can be provided in the form of peripheral grooves or the like at the shank, preferably at the distal area thereof.

The invention claimed is:

1. A medical screw driver for introducing mono-axial or poly-axial pedicle screws into a vertebral body, the medical screw driver comprising:
   a shank which includes, in an area of a proximal end portion of the shank, a first coupling portion for a detachable handling member to apply a torque to the shank and, at a distal end portion of the shank, a screw driver portion is provided that is adapted to be inserted in a corresponding seat at a screw head of a pedicle screw and can transmit a torque applied to the shank to the screw head; and
   a sleeve rotatable relatively about the shank, a distal end portion of the sleeve includes a second coupling portion for coupling with a third coupling portion formed at the screw head of the pedicle screw,
   wherein the sleeve has a multi-part design and comprises a distally arranged first sleeve portion including a first engaging portion, and a second sleeve portion arranged proximally thereto including a complementary second engaging portion, wherein the first engaging portion and the second engaging portion are configured so that both are capable of being made to engage so that the second sleeve portion can transmit a torque to the first sleeve portion so as to couple the second coupling portion provided on the first sleeve portion to the screw head, and that the second sleeve portion is capable of being disengaged from the first sleeve portion in an axial direction, and is capable of being drawn off the shank in a proximal direction without having to release the first sleeve portion from the screw head of the pedicle screw, and wherein the shank includes two jointly mountable shank portions and the first sleeve portion is caught between the shank portions in a mounted condition.

2. The medical screw driver according to claim 1, wherein the first and second engaging portions comprise corresponding crowns which are engaged in the axial direction and constitute a form closure in a circumferential direction for torque transmission.

3. The medical screw driver according to claim 1, wherein the first sleeve portion is supported to be axially movable on the shank at least over a predetermined length, wherein a stop provided at the shank in a distal direction ahead of the screw driver portion restricts an axial degree of freedom of the first sleeve portion so that the first sleeve portion can transmit an axial force to the shank in the distal direction, when the shank is coupled to the screw head of the pedicle screw.

4. The medical screw driver according to claim 1 comprising an outer sleeve, wherein the outer sleeve is rotatable relative to the sleeve and is capable of being detachably applied to the first and/or second sleeve portion for gripping the medical screw driver.

5. The medical screw driver according to claim 4, wherein outer contours of the first sleeve portion and of the second sleeve portion are configured so that the outer sleeve is axially caught between the first sleeve portion and the second sleeve portion.

6. The medical screw driver according to claim 1, wherein the shank has a continuous internal passage in the axial direction; and
at the proximal end portion of the shank a connecting system is provided for connecting a cement applicator to the passage.

7. The medical screw driver according to claim 1, wherein the second sleeve portion is capable of being detachably locked at the shank for axial securing by a locking bar biased in a radial direction and provided at the second sleeve portion, the locking bar automatically engaged in a peripheral groove formed at the shank and forming an axial form closure which is manually detachable.

8. The shank for the medical screw driver according to claim 1, wherein, in said area of said proximal end portion of the shank, the first coupling portion for the detachable handling member is provided for applying a torque to the shank and at the distal end portion of the shank of which the screw driver portion is provided which is adapted to be inserted in a corresponding seat at the screw head of the pedicle screw and can transmit a torque applied to the shank to the screw head, wherein the shank includes a continuous internal passage in the axial direction; and at the proximal end portion of the shank a connecting system is provided to connect a cement applicator to the passage.

9. A method for introducing mono-axial or poly-axial pedicle screws into a vertebral body using a medical screw driver according to claim 1, comprising the steps of:
inserting the screw driver portion in a corresponding seat at the screw head of the pedicle screw;
coupling and bracing the first sleeve portion with the screw head of the pedicle screw and the screw driver portion with the screw head by rotating the second sleeve portion; and
removing the second sleeve portion from the shank in the proximal direction while maintaining the bracing of the first sleeve portion with the screw head and the bracing of the screw driver portion with the screw head.

10. The method according to claim 9, wherein the shank of the medical screw driver includes a continuous internal passage in the axial direction, and a connecting system is provided at the proximal end portion of the shank to connect a cement applicator to the passage;
the method further comprising the steps of:
coupling a cement applicator to the connecting system; and
injecting cement via the passage into the pedicle screw.

11. The method according to claim 9, further comprising the steps of:
arranging distractors and, respectively, compressors on the shank or the first sleeve portion of two or more screw drivers coupled to two or more pedicle screws; and
implementing a distraction or compression.

12. A medical screw driver for introducing mono-axial or poly-axial pedicle screws into a vertebral body, the medical screw driver comprising:
a shank which includes, in an area of a proximal end portion of the shank, a first coupling portion for a detachable handling member to apply a torque to the shank and, at a distal end portion of the shank, a screw driver portion is provided that is adapted to be inserted in a corresponding seat at a screw head of a pedicle screw and can transmit a torque applied to the shank to the screw head; and
a sleeve rotatable relatively about the shank, a distal end portion of the sleeve includes a second coupling portion for coupling with a third coupling portion formed at the screw head of the pedicle screw,
wherein the sleeve has a multi-part design and comprises a distally arranged first sleeve portion including a first engaging portion, and a second sleeve portion arranged proximally thereto including a complementary second engaging portion,
wherein the first engaging portion and the second engaging portion are configured so that both are capable of being made to engage so that the second sleeve portion can transmit a torque to the first sleeve portion so as to couple the second coupling portion provided on the first sleeve portion to the screw head, and that the second sleeve portion is capable of being disengaged from the first sleeve portion in an axial direction, and is capable of being drawn off the shank in a proximal direction without having to release the first sleeve portion from the screw head of the pedicle screw,
wherein the first sleeve portion is supported to be axially movable on the shank at least over a predetermined length, and
wherein a stop provided at the shank in a distal direction ahead of the screw driver portion restricts an axial degree of freedom of the first sleeve portion so that the first sleeve portion can transmit an axial force to the shank in the distal direction, when the shank is coupled to the screw head of the pedicle screw.

13. The medical screw driver according to claim 12, comprising an outer sleeve, wherein the outer sleeve is rotatable relative to the sleeve and is capable of being detachably applied to the first and/or second sleeve portion for gripping the medical screw driver.

14. The medical screw driver according to claim 13, wherein outer contours of the first sleeve portion and of the second sleeve portion are configured so that the outer sleeve is axially caught between the first sleeve portion and the second sleeve portion.

15. The medical screw driver according to claim 12, wherein the shank has a continuous internal passage in the axial direction; and
at the proximal end portion of the shank a connecting system is provided for connecting a cement applicator to the passage.

16. The medical screw driver according to claim 12, wherein the second sleeve portion is capable of being detachably locked at the shank for axial securing by a locking bar biased in a radial direction and provided at the second sleeve portion, the locking bar automatically engaged in a peripheral groove formed at the shank and forming an axial form closure which is manually detachable.

17. A medical screw driver for introducing mono-axial or poly-axial pedicle screws into a vertebral body, the medical screw driver comprising:
a shank which includes, in an area of a proximal end portion of the shank, a first coupling portion for a detachable handling member to apply a torque to the shank and, at a distal end portion of the shank, a screw driver portion is provided that is adapted to be inserted in a corresponding seat at a screw head of a pedicle screw and can transmit a torque applied to the shank to the screw head; and
a sleeve rotatable relatively about the shank, a distal end portion of the sleeve includes a second coupling portion for coupling with a third coupling portion formed at the screw head of the pedicle screw,
wherein the sleeve has a multi-part design and comprises a distally arranged first sleeve portion including a first engaging portion, and a second sleeve portion arranged proximally thereto including a complementary second engaging portion,
wherein the first engaging portion and the second engaging portion are configured so that both are capable of being made to engage so that the second sleeve portion can transmit a torque to the first sleeve portion so as to couple the second coupling portion provided on the first sleeve portion to the screw head, and that the second sleeve portion is capable of being disengaged from the first sleeve portion in an axial direction, and is capable of being drawn off the shank in a proximal direction without having to release the first sleeve portion from the screw head of the pedicle screw,
wherein the first and second engaging portions comprise corresponding crowns which are engaged in the axial direction and constitute a form closure in a circumferential direction for torque transmission, and
wherein the first sleeve portion is supported to be axially movable on the shank at least over a predetermined length, wherein a stop provided at the shank in a distal direction ahead of the screw driver portion restricts an axial degree of freedom of the first sleeve portion so that the first sleeve portion can transmit an axial force to the shank in the distal direction, when the shank is coupled to the screw head of the pedicle screw.

18. The medical screw driver according to claim 17, comprising an outer sleeve, wherein the outer sleeve is rotatable relative to the sleeve and is capable of being detachably applied to the first and/or second sleeve portion for gripping the medical screw driver.

19. The medical screw driver according to claim 18, wherein outer contours of the first sleeve portion and of the second sleeve portion are configured so that the outer sleeve is axially caught between the first sleeve portion and the second sleeve portion.

20. The medical screw driver according to claim 17, wherein the shank has a continuous internal passage in the axial direction; and
at the proximal end portion of the shank a connecting system is provided for connecting a cement applicator to the passage.

21. The medical screw driver according to claim 17, wherein the second sleeve portion is capable of being detachably locked at the shank for axial securing by a locking bar biased in a radial direction and provided at the second sleeve portion, the locking bar automatically engaged in a peripheral groove formed at the shank and forming an axial form closure which is manually detachable.

* * * * *